United States Patent [19]

Le et al.

[11] Patent Number: 5,064,767

[45] Date of Patent: Nov. 12, 1991

[54] CARBOXYL-TERMINAL PROTEIN SEQUENCING METHOD AND KIT

[75] Inventors: Dean A. Le, Menlo Park; Kazuhiko Tatemoto, Stanford, both of Calif.

[73] Assignee: The Board of Trustees of the Leland Stanford Junior University, Stanford, Calif.

[21] Appl. No.: 541,526

[22] Filed: Jun. 21, 1990

[51] Int. Cl.[5] ............................................. G01N 33/68
[52] U.S. Cl. ........................................ 436/89; 422/61; 436/98; 436/111; 436/120; 436/128; 530/345; 530/402; 530/408; 530/409; 530/410
[58] Field of Search ................ 436/89, 111, 120, 128, 436/161, 98; 422/61; 530/345, 402, 410, 408, 409

[56] References Cited

FOREIGN PATENT DOCUMENTS 1-250863 10/1989 Japan ...................................... 436/89

OTHER PUBLICATIONS

Parham et al., Biochem. Biophys. Res. Comm., vol. 80, No. 1, pp. 1-6, 1978.
Loudon et al., Tetrahedron Letters, No. 5, pp. 437-440, 1978.

Primary Examiner—Robert J. Hill, Jr.
Attorney, Agent, or Firm—Bertram I. Rowland

[57] ABSTRACT

Polypeptides are sequenced from the carboxyl terminus by treating the peptide with an iodoxybenzene, followed by removal of the excess reagent and reaction with 2-aminothiophenol at an elevated temperature. The resulting benzthiazolidine is then analyzed to determine the C-terminal amino acid which has been cleaved. A kit which contains the iodoxybenzene and 2-aminothiophenol reagents is separate containers is also disclosed.

9 Claims, 1 Drawing Sheet

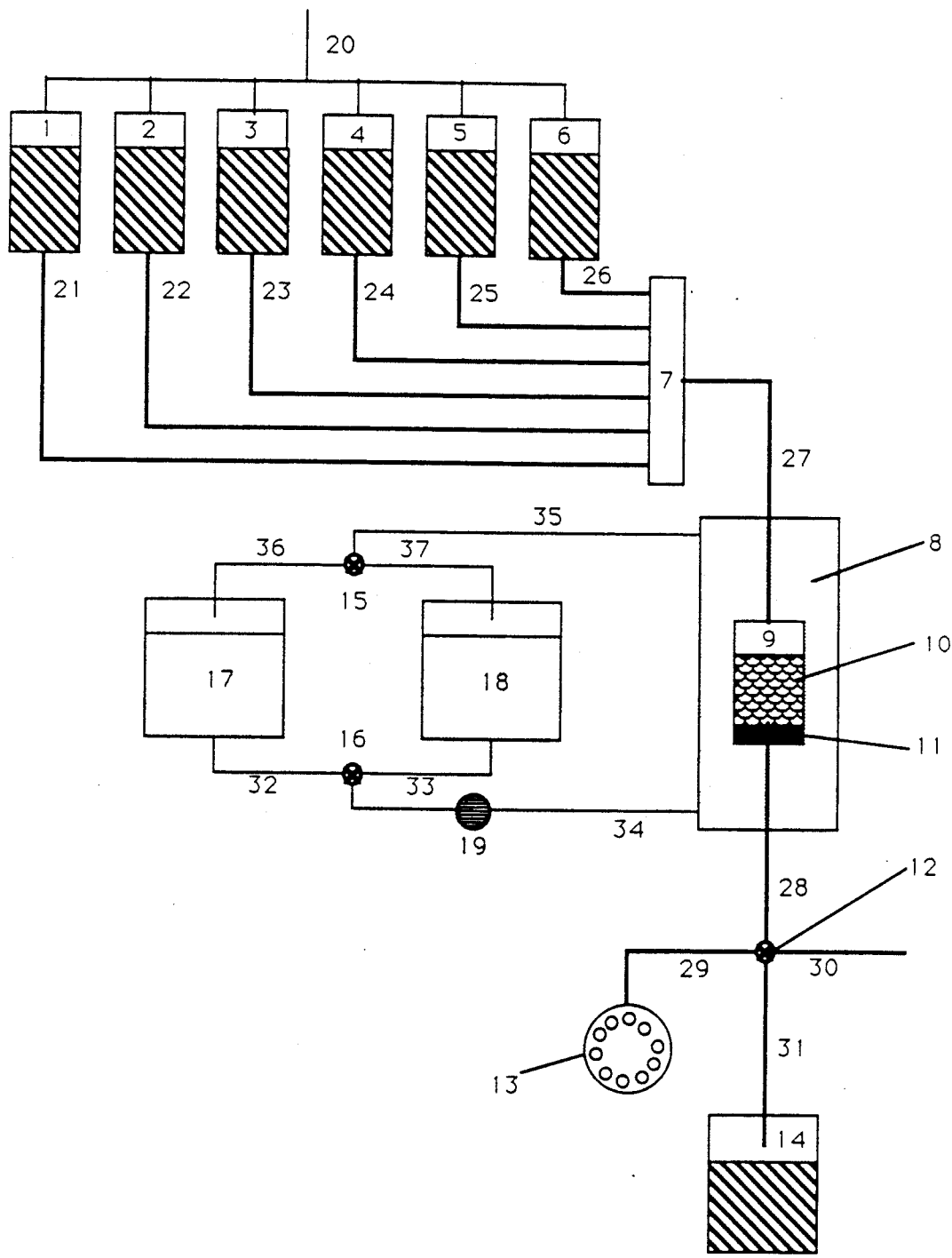

CARBOXYL-TERMINAL PROTEIN SEQUENCING METHOD AND KIT

INTRODUCTION

1. Technical Field

The field of this invention is sequencing of polypeptides.

2. Background

As the biological world unfolds with the isolation of proteins from a vast variety of sources, there is continuing interest in providing new and improved ways for characterizing the proteins. An essential aspect of every protein is its primary structure, its amino acid sequence. For a variety of reasons, the major attention and effort has been directed toward sequencing beginning with the amino-terminal end. For this purpose, automated instrumentation has been provided, where the protein may be bound to a solid surface, and the terminal amino acids removed sequentially, with the released amino acid being detected by a variety of sensors. In this manner, relatively large peptide sequences may be determined.

In many situations, however, there is substantial interest in being able to determine the carboxyl terminal structure. In the case of surface membrane proteins, the cytoplasmic portion is usually carboxy terminal. To understand how the cytoplasmic portion of the surface membrane protein interacts with components in the cell, it would be interesting to be able to rapidly determine what the carboxyl sequence is.

Not infrequently, the terminal amino acid of a polypeptide may be blocked, such as by acetylation or methylation or other functional group. The modification of the terminal amino group interferes with methods of degradation, inhibiting the determination of the sequence from the amino terminus.

Most proteins contain more than 100 residues, well beyond the 50-60 residue limitation of conventional sequencers. In such cases, laborious processes involving protein fragmentation are required for complete structural analysis. The development of an automated C-terminal sequencing method would make it possible to determine sequences of N-terminally-blocked proteins and also to determine directly amino acid sequences of proteins with over 100 residues when combined with the use of conventional N-terminal sequencers. Importantly, when DNA sequence data are available, complete primary structures of expressed protein products can be elucidated by knowing both N- and C- terminal sequences of the proteins.

Relevant Literature

Parham and Loudon, *Biochem. and Biophys. Res. Comm.* (1978) 80:1-6 described the use of bis(I,I-trifluroacetoxy)iodobenzene to modify the C-terminal amide group of a peptide to the amine. Heat treatment results in the cleavage of the C-terminus as the imine derivative from the peptide chain. This amino acid derivative is too unstable to identify by conventional means. Loudon, et al., *JACS*, (1981) 103:4508-4515. Loudon also carried out thermal cleavage of the amine in the presence of water yielding an aldehyde, which was also difficult to identify. Thiazolidine formation between cysteine derivatives and aldehydes has been reported by Kallen, *JACS*, (1971) 93:6227. Conversion of a carboxyl group of an amino acid to an amine by p-nitrophenyl-phosphorylazide has been reported by Parham and Loudon, *Tetrahedron Letters*, (1978) 5:437-440.

SUMMARY OF THE INVENTION

Methods and apparatus are provided for sequential degradation of polypeptides from the C-terminus by attachment of protein to a solid support, side chain protection, amidation of the C-terminal carboxyl group, and sequential degradation employing a reagent capable of rearranging the amide to an amino group, which is cleaved by heat treatment followed by reaction with an aminothiol to form a heterocycle which may be detected by HPLC and other conventional methods. The invention also includes a kit which contains the reagents for the sequential degradation of the polypeptides in separate containers.

BRIEF DESCRIPTION OF THE DRAWINGS

The FIGURE is a diagrammatic view of an apparatus for automatic degradation of a protein from the C-terminus.

DESCRIPTION OF THE SPECIFIC EMBODIMENTS

The subject invention provides a method for carboxyl-terminal sequencing of polypeptides. The method comprises the steps of attachment of the polypeptide to a solid support, protecting side chains of the polypeptide, as appropriate, amidation of the terminal carboxyl group, C-terminal sequential degradation, and detection of the monomeric product released from the chain.

Any polypeptide may be sequenced according to the subject method, where the polypeptide comprises alpha-amino acids. The amino acids may be the naturally occurring L or the unnatural D-stereoisomer or other infrequently encountered amino acid. So long as the amino acids have an alpha-amino group, they may have any other functionality present on the side chain, so as to be natural or unnatural amino acids, where the amino acids may differ from the common 20 naturally occurring amino acids. Usually, the polypeptide will have at least 2 monomeric units and may have a thousand or more monomeric units, the size of the peptide not being significant for the purpose of this invention. Of course, for handling, it may be of interest to hydrolyze the polypeptide to smaller fragments, where the polypeptide is over about 100 amino acids. The hydrolysis may be achieved by employing acid or basic aqueous solutions at moderately elevated temperatures, by employing enzymes, such as trypsin or chymotrypsin, using cyanogen bromide to cleave at methionine residues, or the like.

The polypeptide sample may be subject to a variety of pretreatments, such as removal of any sugars, employing enzymes, or the sugar groups may be retained as protective groups, if desired. Depending upon the source of the peptide, the sample may be subject to a variety of pretreatments, such as extraction, affinity purification, HPLC, or the like.

The first step is the linking of the peptide to a solid support. Any convenient solid support which does not interfere with the progress of the sequential degradation may be employed. Supports include control pore glass, Pyrex, polystyrene beads, latex beads, agarose, glass fibre membranes, nitrocellulose membranes, or the like. A number of materials are commercially available and the same types of materials which have been used for N-terminal sequential degradation may be employed in the subject invention.

The peptide may be bound either covalently or non-covalently to the support, usually covalently. The support may have any of a wide variety of functionalities which are capable of forming a covalent bond with any of the functionalities present on the N-terminal amino group or the side chain of the amino acids. Thus, the active group may be a group which reacts with amino, thiol, or hydroxyl. For the most part, the group will be reactive with an amino group to form a stable bond. Functionalities which may be employed include imino acids, activated carboxyl groups, such as N-succinimide esters, p-nitrophenyl esters, pentafluorophenyl esters, etc., carbodiimide, reductive amination with aldehydes, or the like. It is not essential that the terminal amino group is the only functionality attached to the support. To the extent, the amino groups of lysine are involved in bonding to the support, the sequential degradation will continue through that amino acid. Where all of the particular amino acid has become bonded to the support, then there will be an absence of amino acid being released during that cycle. Where only a portion of the particular amino acid is bound, then the amount of that amino acid which is bonded will be diminished. Since for conjugation of the amino group, for the most part only lysine will be involved, lysine can be readily detected by the subject invention.

The reaction will normally occur in aqueous medium, where the protein is dispersed in the aqueous medium at a convenient pH which allows for the polypeptide to react with the activated surface in accordance with conventional techniques. See, for example, H.H. Weetall, *Methods in Enzymology*, 44,135 (1976).

After attachment of the protein to the solid support, the side chains are protected by any convenient means. Various functionalities may be employed for protection of the available functionalities. Thus, hydroxyl groups may be esterified, with carboxylic acid anhydrides or acyl halides, conveniently acetic anhydride. Etherification reagents include trityl, dianisylmethyl halide, phenacyl halide, tert-butyl halide, benzoyl chloride, or the like. Conditions for the reaction are conventional and need not be described here. See, for example, A.N. Glaser, Laboratory Techniques in Biochemistry and Molecular Biobology, 4, 1–120 (1976).

After the polypeptide has been protected, the terminal carboxyl group is amidated. Conveniently, an amino acid amide is employed for the amidation, more particularly glycine amide. The carboxyl group may be conveniently activated with anhydride or a carbodiimide. Conventional carbodiimides include 1-ethyl-3-(3'-dimethylaminopropyl)carbodiimide or N,N'-dicyclohexylcarbodiimide. Conditions usually employ an aqueous medium in which the solid support is immersed, comprising the carbodiimide, a convenient buffer and the amino acid amide. Alternatively, the mixed anhydride or activated ester can be formed for reaction with the carboxyl group.

Once the terminal carboxyl group has been amidated, it may then be subject to sequential degradation. Each cycle of C-terminal sequential peptide degradation consists of two steps: first, modification of the C-terminal amide group to the amine; and second, thermal cleavage of the modified residue from the parent molecule in the presence of an aminothiol to produce a heterocyclic compound for analysis.

In the first step, a compound is employed which provides for rearrangement of the carboxamide to an amino group to produce a geminal-diamino compound, where one of the nitrogens is bonded to the remainder of the peptic chain. Various reagents may be employed, particularly an aryliodonium compound. Compounds of interest which may be used include bis(I,I-trifluoroacetoxy)iodobenzene. The conditions for the reaction are at room temperature in aqueous solution.

After the reaction to form the geminal diamino group, the terminal residue is thermally cleaved at an elevated temperature of at least about 60° C. in the presence of a solution of an aminothiol, particularly an ortho-thioarylamine. Particularly useful is 2-aminothiophenol. This compound is found to produce a thiazolidine derivative with the cleaved product, which is stable at elevated temperatures and over a wide pH range. It has light absorption at 310 nm, which conveniently can be used for the detection of cleaved products by HPLC in picomolar ranges.

The resulting residue from the peptide may then be analyzed as indicated above by HPLC or any other convenient technique, such as mass spectrometry, gas chromatography, paper chromatography, or the like.

The FIGURE provides a diagrammatic view of an apparatus which could be used in accordance with the subject invention. The apparatus comprises reaction chamber 9, which has a peptide sample attached to a solid support 10, a filter disk 11 near the bottom, and water jacket 8. Inlet 27 is connected to one side of manifold valve 7. Reservoirs 1, 2 store the solutions for washing and sample collection and are connected to the reaction chamber 9 through conduit 21,22, respectively. Reagent reservoirs 3–6 are also provided for storing reagents which are fed to the other side of manifold valve 7 through conduit 23–26, respectively. By appropriate manipulation of manifold valve 7, measured amounts of the solutions may be introduced into reaction chamber 9. The wash and reagent solutions are introduced to the reaction chamber 9 by applying a mild pressure from an inert gas tube through conduit 20. The solution containing the cleaved product is introduced to fraction collector 13 after each cycle through outlet 28, valve 12, and conduit 29. Waste receiver 14 is fitted with outlet 28, valve 12 and conduit 31. Conduit 30 is connected to a vacuum line and can be used for evacuating reaction chamber 9 via outlet 28 and valve 12. The temperature of reaction chamber 9 is rapidly changed from 23° C. to 100° C. during the cleavage reaction by circulating a hot liquid from water bath 17 through conduit 32, valve 16, pump 19, conduit 34, 35, valve 15, and conduit 36. Otherwise, the temperature of the reaction chamber 9 is maintained at 23° C. by circulating a liquid from water bath 18 through conduit 33, valve 16, pump 19, conduit 34, 35, valve 15, and conduit 37. All valves may be manually or automatically controlled.

For example, after the peptide sample bound to a solid support is placed in reaction chamber 9, the C-terminus of the attached peptide may be amidated by the addition of a solution containing glycine amide and carbodiimide from reservoir 3. After the reaction is complete, the chamber is washed with a wash solution from reservoir 1. The wash solution is exhausted into waste receiver 14. The side chains of the peptide may then be modified by an acylating reagent from reservoir 4. After the reaction is complete, the chamber is washed again with a wash solution from reservoir 1. The C-terminal modifying reagent may then be added from reservoir 5 and the reaction allowed to go to completion. After washing with wash solution from reservoir 1, the peptide sample is dried by vacuum via conduit 30. 2-amino-thiophenol solution from reservoir 6 is then added and the chamber is rapidly heated and shortly after, rapidly cooled down by means of circulating a hot and cold liquid into water jacket 8. After completion of the reaction, the solution is transferred to fraction collector 13 by sample collection solution delivered from reservoir 2. The cleaved products obtained after each cycle of the degradation are analyzed by HPLC.

The following examples are offered by way of illustration and not by way of limitation.

EXPERIMENTAL

MATERIALS AND METHODS 2-aminothiophenol (99%, Aldrich Co.) was distilled twice in vacuo until a colorless product was obtained and stored under nitrogen gas in a freezer. Bis-(trifluoroacetoxy)iodobenzene (TIB) was synthesized as described (Parham, M.E. and Loudon G. M., Biochem. Biophys. Res. Commun., 80, 1-6, 1978). The standards of BZT-Leu, BZT-Ala, BZT-Gly, and BZT-Val (BZT-benzothiazolidine) were prepared after mixing the respective aldehydes (4 parts by volume): isovaleraldehyde, acetaldehyde, formaldehyde, and isobutyraldehyde, with 2-aminothiophenol (one part by volume) for 30 min at room temperature. The synthetic peptides, [Ala24] secretin 22-27 (Leu-Leu-Ala-Gly-Leu-Val-NH2), its derivative, 3,5-dinitrobenzoyl-Leu-Leu-Ala-Gly-Leu-Val-NH2, and amyloid A4 protein 624-630 (Gly-Ala-Ile-Ile-Gly-Leu-Met-OH) were synthesized manually using N-$\alpha$ Fmoc amino acids in a solid-phase peptide synthesizer.

High performance liquid chromatographic (HPLC) analysis was carried out using a Waters HPLC System at 310 nm detection wavelength using a solvent system, acetonitrile/water/0.1% trifluoroacetic acid.

RESULTS

Liquid-phase sequencing of 3,5-dinitrobenzoyl-leucyl-leucyl-alanyl-glycyl-leucyl-valylamide.

Five $\mu$moles (4 mg) of 3,5-dinitrobenzoyl-Leu-Leu-Ala-Gly-Leu-Val-NH2 was reacted with four-fold equivalents (11 mg) of bis(trifluoroacetoxy)iodobenzene (TIB) in 200 $\mu$l of a solution containing dimethylformamide (50%) and 0.1% trifluoroacetic acid in water (50%). The mixture was kept at room temperature for 6 hours. The reaction was then terminated by adding 1 $\mu$l of hydrazine monohydrate (4-fold equivalents). Since bis(trifluoroacetoxy)iodobenzene reacted rapidly with hydrazine to form nitrogen gas and iodobenzene (Pilair and Nair (1975) Talanta (TIB) 22, 57-60), the excess reagent was eliminated by addition of hydrazine followed by evaporation in vacuo. The modified peptide was purified by HPLC. The fraction containing the modified peptide was collected and dried in vacuo. The modified peptide was then heated in a solution containing 4-fold excess of 2-aminothiophenol in dimethylformamide at 100° C. for 10 minutes. The reaction mixture was then subjected to HPLC analysis. In this HPLC, two major products, besides excess 2-aminothiophenol, were seen. One of the products was the peptide with one less residue from the C-terminus and the other, the benzothiazolidine adduct from the cleaved C-terminal residue. The peptide fraction after the cleavage was collected by HPLC and was subjected to the next cycle of sequencing using the same procedure above mentioned. As little as 0.5 nmoles of the modified peptide can be cleaved and the C-terminal residue can be identified. Cleavage of the first C-terminal residue yielded BZT-Val and 3,5-dinitrobenzoyl-leucyl-leucyl-alanyl-glycylleucylamide. Cleavage of the second yielded BZT-Leu and 3,5-dinitrobenzoyl-leucyl-leucyl-alanylglycylamide, the third, BZT-Gly and 3,5-dinitrobenzoyl-leucyl-leucyl-alanylamide, the fouth, BZT-Ala and 3,5-dinitrobenzoyl-leucyl-leucylamide, the fifth, BZT-Leu and 3,5-dinitrobenzoyl-leucylamide, and finally, the sixth, BZT-Leu and 3,5-dinitrobenzoylamide. When the cleavage at the third cycle was carried out in water according to the method of Loudon and Parham, supra, we observed the formation of at least 4 different peptide products, while a single peptide product was seen at the same cycle by the subject method. The HPLC analysis indicated that the yields of the modification and cleavage reactions were over 90% at each cycle.

Solid-phase sequencing of leucyl-leucyl-alanyl-glvcyl-leucyl-valylamide.

The carboxyl groups of the solid-phase resin PepSyn K (Milligen, Bedford, Mass.) with a N-ethylsuccinate spacer was activated by N-hydroxysuccinimide and N,N-diisopropylcarbodiimide (DIC). About 1 mg of the peptide (1 $\mu$mole) was added to 10 mg of the activated solid support in 40 $\mu$l of dimethylformamide. After the couping, 1.5 mg of PepSyn K containing about 20 nmoles of the peptide was reacted with bis-(trifluoroacetoxy)iodobenzene (3 $\mu$mol) in 15 $\mu$l of a solution of DMF/0.1%TFA (1:1) for 2 hours at 37° C. The resin was washed thoroughly with 95% ethanol and was dried in vacuo. 2 $\mu$l of the cleavage solution containing 0.05 M 2-aminothiophenol and 0.1% trifluoroacetic acid in DMF was added to the resin and the mixture was heated at 100° C. for 10 minutes. After separating the products from the resin by filtration, the resin was washed thoroughly with 95% ethanol and was dried in vacuo. The products were analyzed by HPLC and the resin was subjected to the next sequencing cycle. The cleaved product after each cycle was identified by HPLC using the synthetic BZT derivatives. The complete amino acid sequence of the hexapeptide was determined with a repetitive yield of 87%. Few side products appeared to be produced during the degradation reactions, since the background of the HPLC from each cycle was exceptionally clean. There were about 4% "carry-over" and 4% "spill-over" of the amino acids at each cycle. This "carry-over" was due to incomplete modification of the C-terminus by TIB, whereas the "spill over" was due to partial cleavage of the modified C-terminus during the modification by TIB. Further studies on the optimal reaction conditions would help to minimize these "spill over" and "carry over" of amino acids.

C-terminal amidation of gylcyl-alanyl-isoleucyl-isoleucyl-glycyl-leucyl-methionine The C-terminal amidation of the amyloid A4 fragment was carried out using a solid-phase resin, PepSyn K containing the N-hydroxysuccinimide active ester. 2 mg of the peptide (ca. 3.5 $\mu$moles) in 0.6 ml dimethylformamide (DMF) containing 2% triethylamine was coupled to 100 mg of the resin overnight. The coupling efficiency, based on amino acid analysis data, was 31 μmoles of the peptide per gram of the resin. Since the C-terminal carboxamide group is required for the C-terminal sequencing, glycine amide was attached to the C-terminus of the peptide by the following procedure. 2 μl of diisopropylcarbodiimide (4 equivalents), 3.8 mg of hydroxybenzotriazole (8 equivalents), 4.6 mg of glycine amide, 7 μl of triethylamine in 0.6 ml DMF were added to about 3.1 μmoles of the peptide (1 equivalent) linked to 100 mg of the solid support. The mixture was gently stirred at room temperature overnight. Amino acid analysis indicated that most of the carboxyl group of the peptide linked to the resin was coupled to glycine amide.

It is evident from the above results that the subject method provides for a convenient and efficient method for sequencing a peptide at the carboxyl terminus of the peptide. The benzthiazolidine product may be readily detected by a variety of analytical techniques.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for carboxyl terminal sequencing of peptides, said method comprising:
    having protective groups on other available functionalities with an aryliodonium compound, whereby a geminaldiamino group is formed at the carboxyl terminus of the polypeptide;
    heating the polypeptide in the presence of a vicinal aminothiol to produce a thiazolidine having a side group derived from the carboxyl terminal amino acid of the polypeptide; and
    determining the composition of the thiazolidine, to determine the carboxyl terminal amino acid of said polypeptide.

2. A method according to claim 1, wherein said vicinal aminothiol is o-aminothiophenol and said aryl iodonium compound is bis-(I,I-trifluoracetoxy)iodobenzene.

3. A method according to claim 1, wherein said polypeptide is bound to a solid support at its amino terminus.

4. A method according to claim 3, wherein at least one side-chain amino group is also bound to said solid support.

5. A method according to claim 1, wherein said determining is by high pressure liquid chromatography.

6. A method according to claim 1, wherein said terminal amide is formed by reacting said polypeptide with glycinamide.

7. A method for carboxyl terminal sequencing of peptides, said method comprising:
    bonding a sample polypeptide at its amino groups to an activated solid support;
    protecting other available functional groups other than carboxyl groups;
    activating the carboxyl group at the carboxyl terminus of the polypeptide and reacting the activated carboxyl group with glycinamide to provide a modified polypeptide having a terminal amide at its carboxyl terminus;
    reacting the modified polypeptide with an aryl iodonium compound, whereby a geminal-diamino group is formed at its carboxyl terminus;
    heating the modified polypeptide in the presence of o-aminothiophenol to produce a thiazolidine having a side group derived from the carboxyl terminal amino acid of the polypeptide; and
    determining the composition of the thiazolidine, to determine the carboxyl terminal amino acid of said polypeptide.

8. A method according to claim 7, wherein said aryl iodonium compound is bis-(I,I-trifluoroacetoxy)iodobenzene.

9. A kit for use in a method according to claim 1, said kit comprising bis-(I,I-trifluoracetoxy)iodobenzene and o-aminothiophenol in separate containers.

* * * * *

UNITED STATES PATENT AND TRADEMARK OFFICE
CERTIFICATE OF CORRECTION

PATENT NO. : 5,064,767

DATED : November 12, 1991

INVENTOR(S) : DEAN A. LE; KAZUHIKO TATEMOTO

It is certified that error appears in the above-indentified patent and that said Letters Patent is hereby corrected as shown below:

Column 1, line 4:
    --This invention was made with Government support under PHS Grant No. R01-DK-39188-03. The Government has certain rights in this invention.--

Signed and Sealed this

Twenty-ninth Day of November, 1994

Attest:

BRUCE LEHMAN

Attesting Officer

Commissioner of Patents and Trademarks